United States Patent
French et al.

(10) Patent No.: US 6,723,039 B2
(45) Date of Patent: Apr. 20, 2004

(54) METHODS, SYSTEMS AND DEVICES RELATING TO IMPLANTABLE FLUID PUMPS

(75) Inventors: Ronald French, Santa Clara, CA (US); Bernard H. Andreas, Redwood City, CA (US); Hanson S. Gifford, III, Woodside, CA (US)

(73) Assignee: The Foundry, Inc., Redwood City, CA (US)

( * ) Notice: Subject to any disclaimer, the term of this patent is extended or adjusted under 35 U.S.C. 154(b) by 263 days.

(21) Appl. No.: 09/844,446

(22) Filed: Apr. 27, 2001

(65) Prior Publication Data

US 2002/0161274 A1 Oct. 31, 2002

(51) Int. Cl.⁷ .................................. A61M 1/12
(52) U.S. Cl. ........................................... 600/16
(58) Field of Search .................... 600/16–18; 623/3.1

(56) References Cited

U.S. PATENT DOCUMENTS

| | | | | |
|---|---|---|---|---|
| 3,608,088 A | * | 9/1971 | Dorman et al. ............ 623/3.13 |
| 4,135,253 A | * | 1/1979 | Reich et al. ............... 623/3.13 |
| 5,449,342 A | * | 9/1995 | Hirose et al. .............. 604/6.11 |
| 5,722,930 A | * | 3/1998 | Larson et al. ................ 600/16 |
| 5,762,599 A | * | 6/1998 | Sohn ........................... 600/30 |
| 6,530,876 B1 | * | 3/2003 | Spence ........................ 600/16 |
| 2001/0039369 A1 | * | 11/2001 | Terentiev .................... 600/16 |

* cited by examiner

Primary Examiner—Kennedy Schaetzle
Assistant Examiner—Kristen Droesch
(74) Attorney, Agent, or Firm—Townsend and Townsend and Crew LLP

(57) ABSTRACT

An implantable pump system including an external driver. The implantable pump is driven by the external driver during normal operation but may also operate on a battery. The external driver is used to drive the pump with the mechanical energy of the impeller also being used to charge the battery. The external driver is also useful during emergency situations to directly drive the pump if the battery or internal coils should fail. The pump is also preferably implanted in a subpectoral location outside the patient's rib cage.

8 Claims, 7 Drawing Sheets

US 6,723,039 B2

METHODS, SYSTEMS AND DEVICES RELATING TO IMPLANTABLE FLUID PUMPS

BACKGROUND OF THE INVENTION

The present invention is directed to implantable pumps, pump systems and methods of use. A particular use of the present invention is described for pumping blood; however, the invention may be used for any other purpose without departing from the scope of the invention. For example, the pump may be used for drug infusion or as a spinal fluid pump.

Conventional implantable blood pumps often include a pumping element having magnets attached thereto. The magnets are driven by magnetic forces produced by coils positioned around the pumping element. A battery powers the coils. The battery can be recharged from an external source using a transcutaneous energy transfer (TET) system having external TET coils and internal TET coils. An electrical current is directed through the external TET coils to produce a magnetic field, which impinges on the internal TET coils thereby inducing electrical power generation at the internal coils for charging the battery.

The present invention is directed to improved methods, systems and devices related to implantable pumps.

SUMMARY OF THE INVENTION

In a first aspect of the invention, the pump system has an external driver, which drives the pumping element, such as an impeller, with a direct magnetic coupling. The external driver may be static coils which are charged appropriately or rotating magnets. A battery may also be provided which supplies power to run the pumping element when the external driver is not being used. The external driver provides the ability for emergency operation of the pump if the battery, or some other part of the electrical system, should fail.

In another aspect of the present invention, the battery is recharged by generating electricity from the mechanical energy of the pumping element. The energy is preferably generated at the internal coils, which drive the pumping element when the battery is being used. Use of the internal coils for generating energy to power the battery obviates the need to provide an independent set of internal TET coils as is required in many prior art systems as described above.

The present invention is also directed to methods of pumping blood in a patient. In particular, the present invention is directed to methods of providing partial circulatory support. In another aspect of the present invention, the pump is preferably implanted at a subpectoral location outside the patient's ribs. This location for the pump may be less traumatic to surgically implant than a pump mounted within the chest. The battery may be implanted subpectorally and outside the patient's ribs on the other side of the patient's chest.

The present invention is also directed to methods for pumping blood in a patient. A blood pump having a pumping element, a blood inlet, a blood inlet lumen and a blood outlet is implanted into a patient. The blood inlet is coupled to a first vascular location with the blood inlet lumen extending through the right atrium, through the atrial septum and into the left atrium. The blood inlet may be coupled to any suitable vessel such as a femoral or subclavian vein. The blood outlet may also be coupled to any suitable vessel such as the femoral or subclavian arteries.

These and other aspects of the present invention will become apparent from the description of the preferred embodiment.

DESCRIPTION OF THE PREFERRED EMBODIMENTS

The present invention is directed to implantable pumps, systems and methods of use. Although the invention is described in connection with a preferred embodiment, it is understood that many aspects of the invention may be practiced for pumping any fluid in the body at any location. In a preferred embodiment, blood is pumped to provide the heart with pumping assistance. Although the pump is preferably designed to provide pumping assistance for the heart, various aspects of the invention are applicable for an artificial heart, which maintains complete circulatory support.

Figure 1:
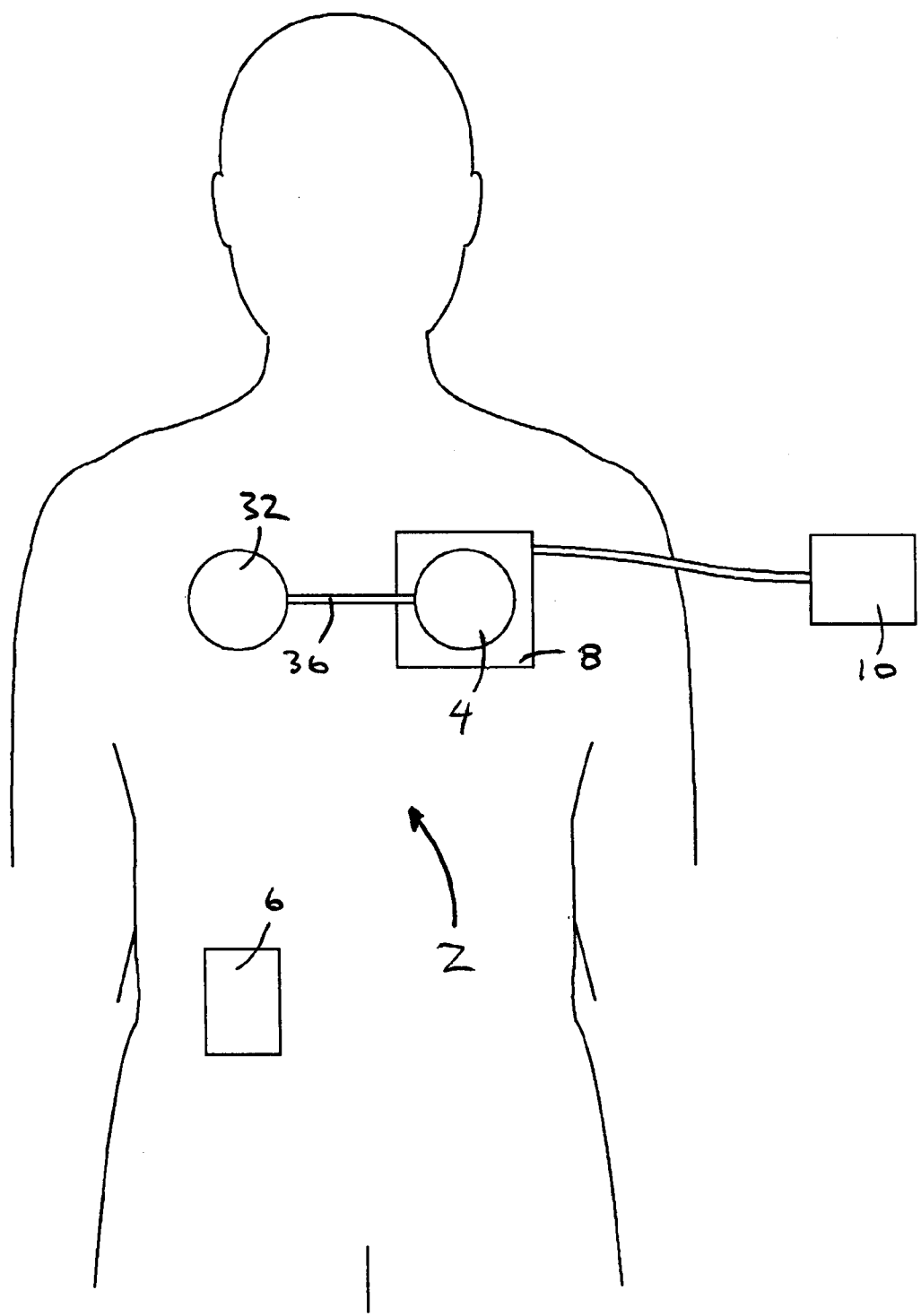
FIG. 1 shows a schematic view of the system with the pump implanted into a patient.
Figure 2:
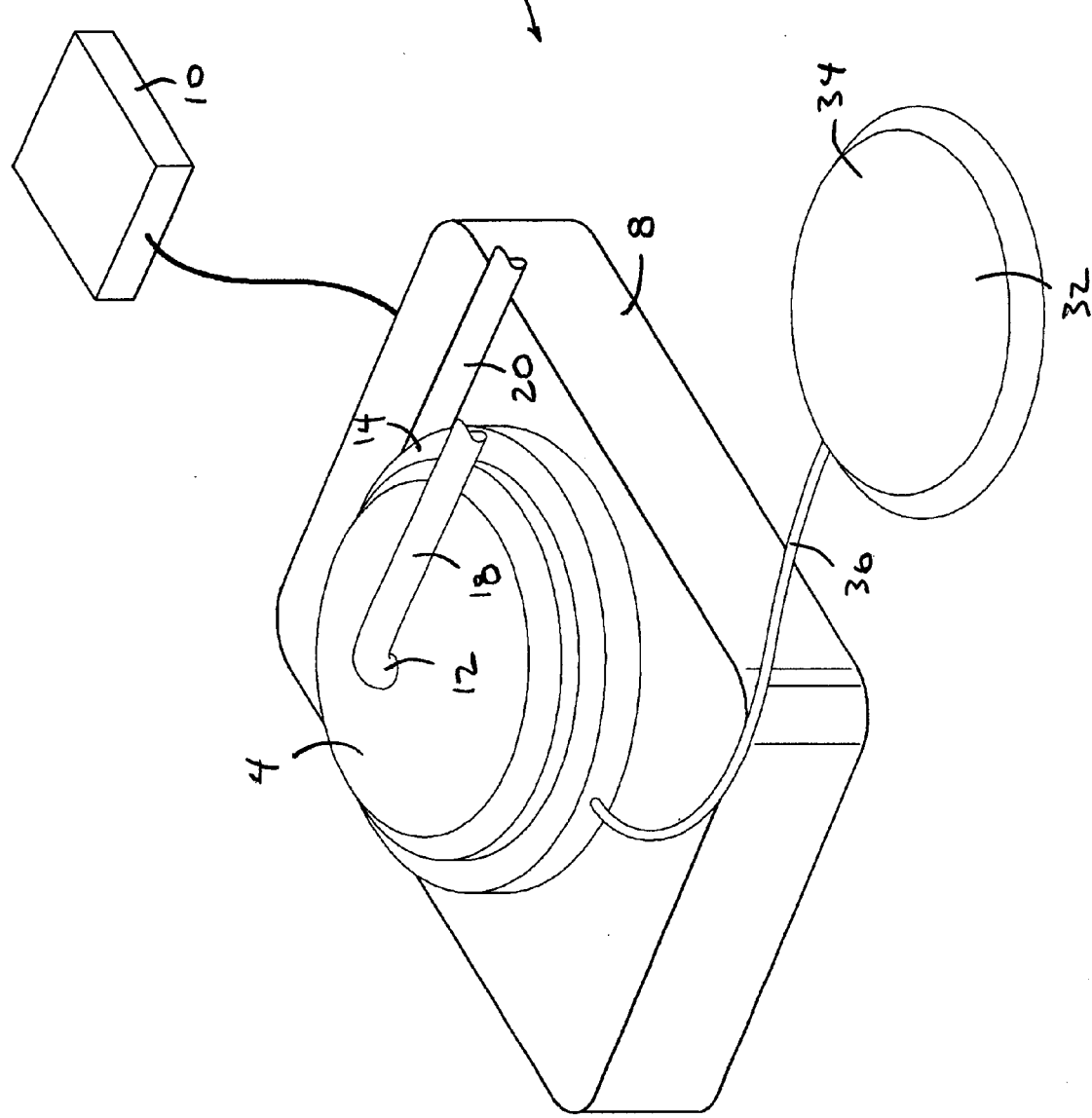
FIG. 2 shows the pump and system of the present invention.
Figure 3:
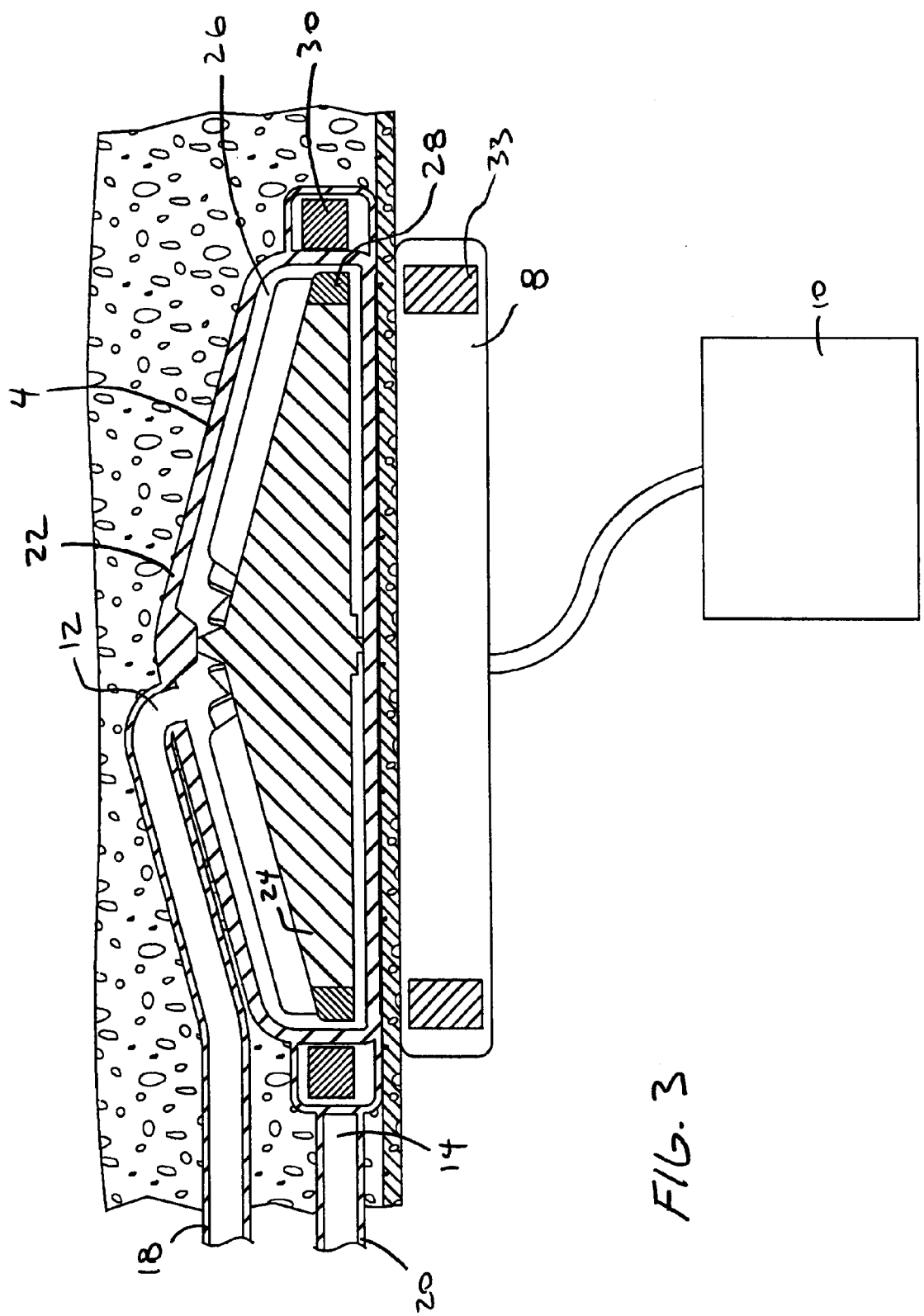
FIG. 3 is a cross-sectional view of the pump with a schematic view of the external driver.

Referring to FIGS. 1–3, a pump system 2 includes an implantable pump 4, an information system 6, and an external driver 8. The driver 8 has a controller 10, which controls the driver 8 as explained below. The pump 4 preferably does not have any leads or the like which penetrate the patient's skin. Of course, various aspects of the invention may be practiced with electrical lines or tubes penetrating the patient's skin.

The implantable pump 4 has a blood inlet 12, a blood outlet 14 and a pumping element, such as an impeller 24, to pump the fluid. The pump 4 has an inlet lumen 18 and an outlet lumen 20, which may be artificial graft material or a harvested vessel, coupled to the inlet and outlet 12, 14, respectively. The inlet and outlet lumens 18, 20 are attached to suitable vascular locations such as the locations described below. The pumping element may comprise any one of a variety of conventional pump types, such as a roller pump, axial pump, centrifugal pump, or any other suitable pump, without departing from the scope of the invention. For example, suitable pumps include the Thoratec HeartMate LVAD and the MedQuest HeartQuest VAD.

Referring to FIG. 3, the pump 4 is a centrifugal pump 22 having an impeller 24 to pump fluid passing through a fluid chamber 26. The impeller 24 has magnets 28 attached thereto. The impeller 24 is driven by magnetic forces acting on the magnets 28 produced by an external driver 33 or internal coils 30. The internal coils 30 are powered by a battery 32 contained in a separate housing 34 with electrical lines contained in a conduit 36 between the pump 4 and battery 32. Of course, the battery 32 may be coupled to the pump 4 or contained within the same housing without departing from the scope of the invention. Furthermore, the pump 4 and system 2 may include more than one battery 32 for additional safety and extended operation.

During normal operation, the implantable pump 4 is driven directly by the external driver 8. An advantage of the pump and system of the present invention is that the pump can still operate with the driver 8 even if the electrical system or battery 32 fails. Many conventional systems cannot operate and/or charge the battery 32 if either the internal TET coils or battery 32 fails. The external driver 8 has a magnetic field generating element 33, such as coils or magnets, which produce a magnetic field which acts on the magnets 28 on the impeller 24 to drive the impeller 24. The direct magnetic coupling between the external driver 8 and impeller 24 provides various advantages as described herein.

In an aspect of the invention, the battery 32 may be used by itself to run the pump by charging the internal coils 30. When the battery 32 or batteries are running low, a signal may be generated which indicates that the battery 32 must be recharged. The signal may be given to the user in any suitable manner. For example, the information unit 6 carried by the user may be used to indicate low battery charge. Alternatively, the external driver 8 and/or control system 10 may be used to alert the user that the battery 32 is running low.

In still another aspect of the invention, the mechanical energy of the pumping element, such as the impeller 24, is used to generate power to charge the battery 32. The impeller 24 preferably induces electrical energy at the internal coils 30, which is then used to recharge the battery 32. An advantage of the present invention is that a separate set of internal TET coils is not required to charge the battery since the impeller 24 is driven directly by the external driver 8 and the internal coils 30 are used with the impeller 24 to charge the battery. Elimination of the internal TET coils can also reduce the size, cost and complexity of the pump.

The implantable pump 4 may be implanted in the patient's body for any purpose. Various aspects of the invention are, however, directed to specific methods and systems for pumping blood in a patient. In a first aspect, the implantable pump 4 is implanted subpectorally and outside the patient's rib cage (see FIG. 1). Implantation at this position provides proximity to the heart and great vessels while also obviating the need to open the patient's ribcage. The battery 32 may also be implanted on the other side of the patient's chest in a subpectoral location outside the patient's rib cage. Of course, the pump 4 may also be positioned in other locations and the battery 32 may be contained in the same housing as the pump 4 without departing from many aspects of the invention.

Figure 4:
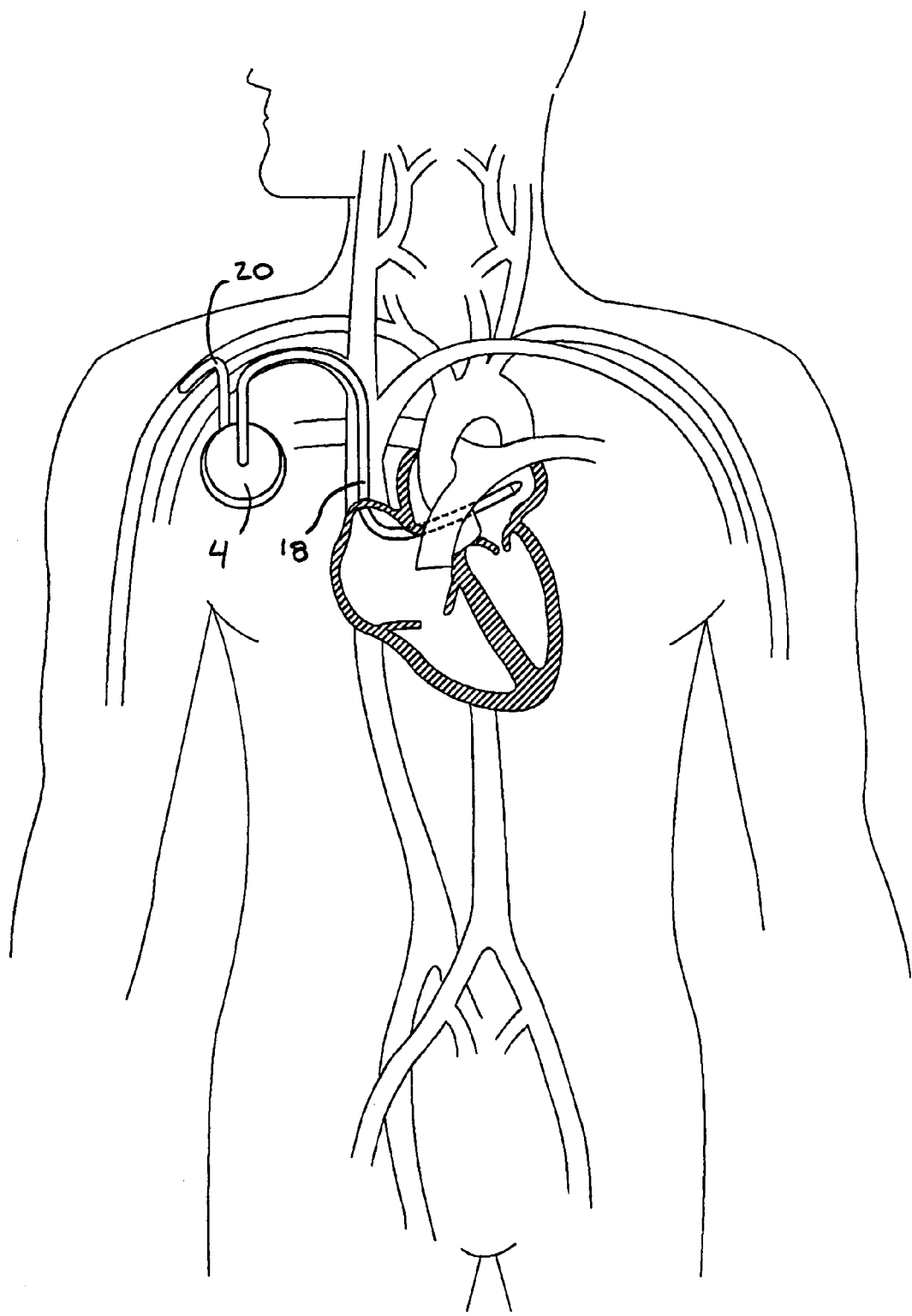
FIG. 4 shows the schematic of FIG. 1 with the pump outlet coupled to the right subclavian artery and the pump inlet coupled to a conduit passing through the SVC, into the right atrium and into the left atrium via the atrial septum.
Figure 7:
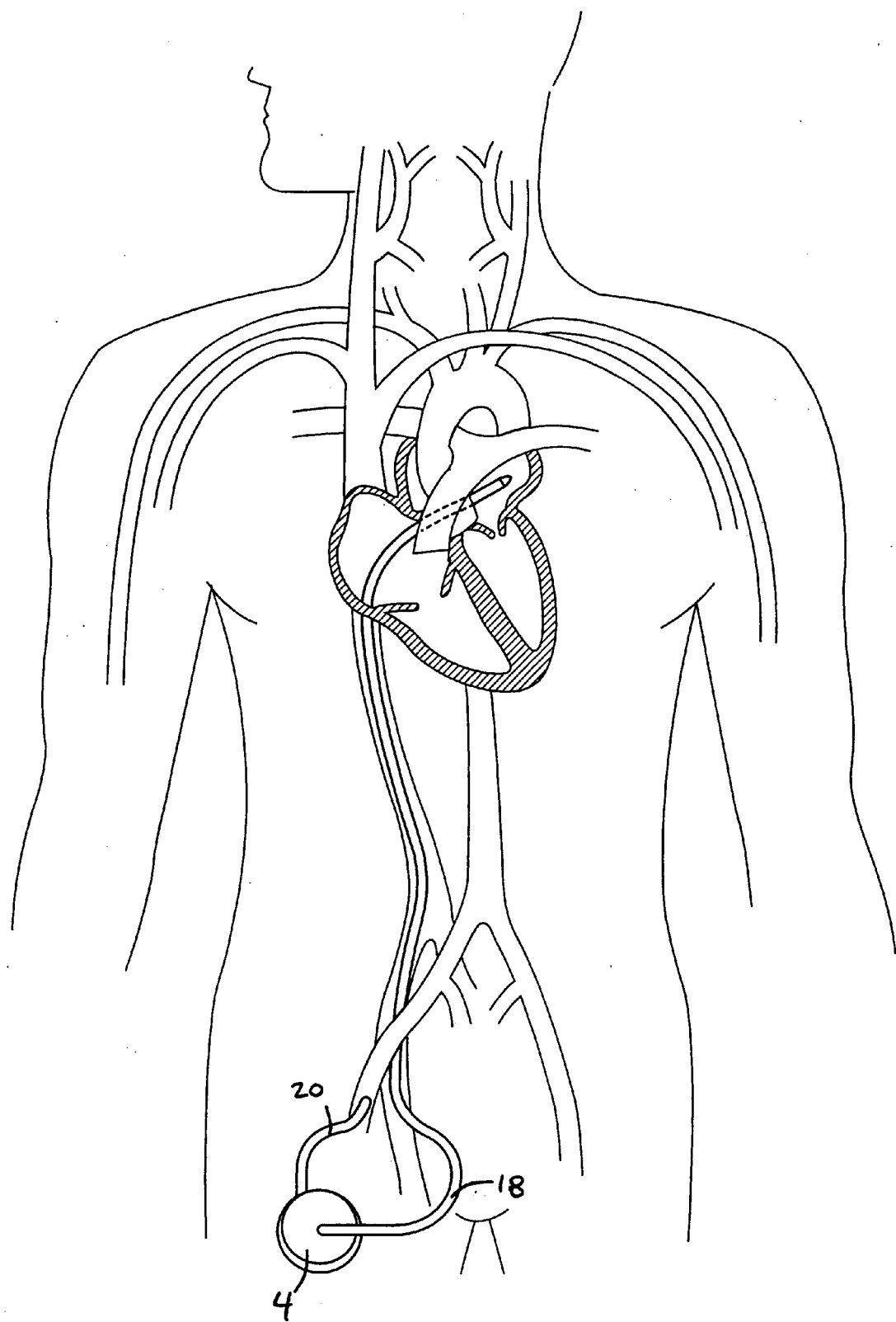
FIG. 7 shows the schematic of FIG. 1 with the pump implanted in the groin and pump outlet coupled to a femoral artery and the pump inlet extending through a femoral vein, into the right atrium and then into the left atrium via the atrial septum.

In another aspect of the present invention, the implantable pump 4 is preferably implanted in the following manner. Referring to FIG. 4, the inlet lumen 18 draws blood from the left atrium. The inlet lumen passes through a penetration in the right axillary or subclavian vein and then down the superior vena cava to the right atrium. The inlet lumen 18 then passes through the atrial septum to the left atrium. FIG. 7 shows the inlet lumen 18 passing through a penetration in a femoral vein and then extending through the right atrium, atrial septum and into the left atrium.

Figure 5:
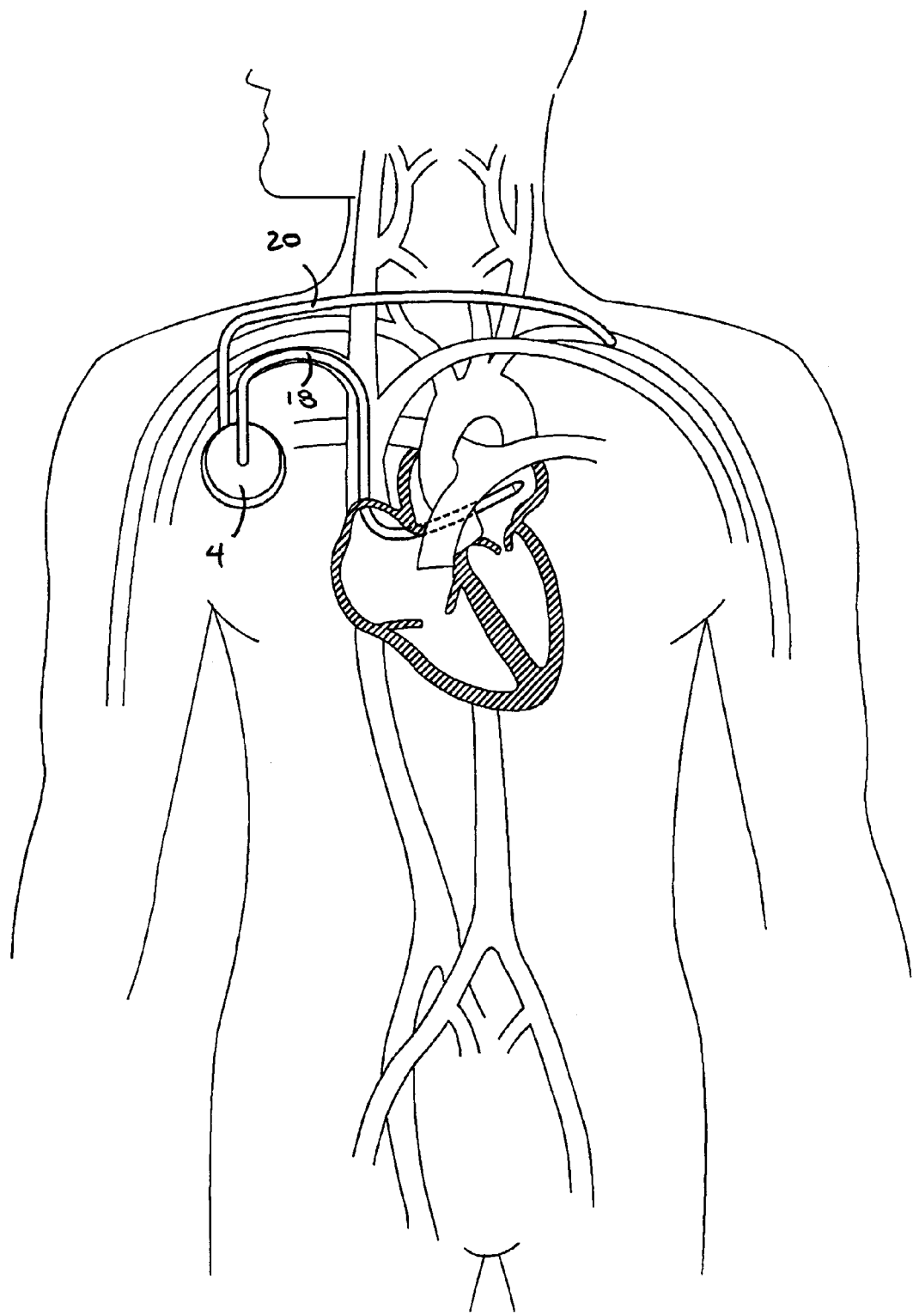
FIG. 5 shows the schematic of FIG. 1 with the pump mounted on the right side of the chest and the pump outlet coupled to the left subclavian artery and the pump inlet coupled to a conduit passing through the SVC, into the right atrium and into the left atrium via the atrial septum.
Figure 6:
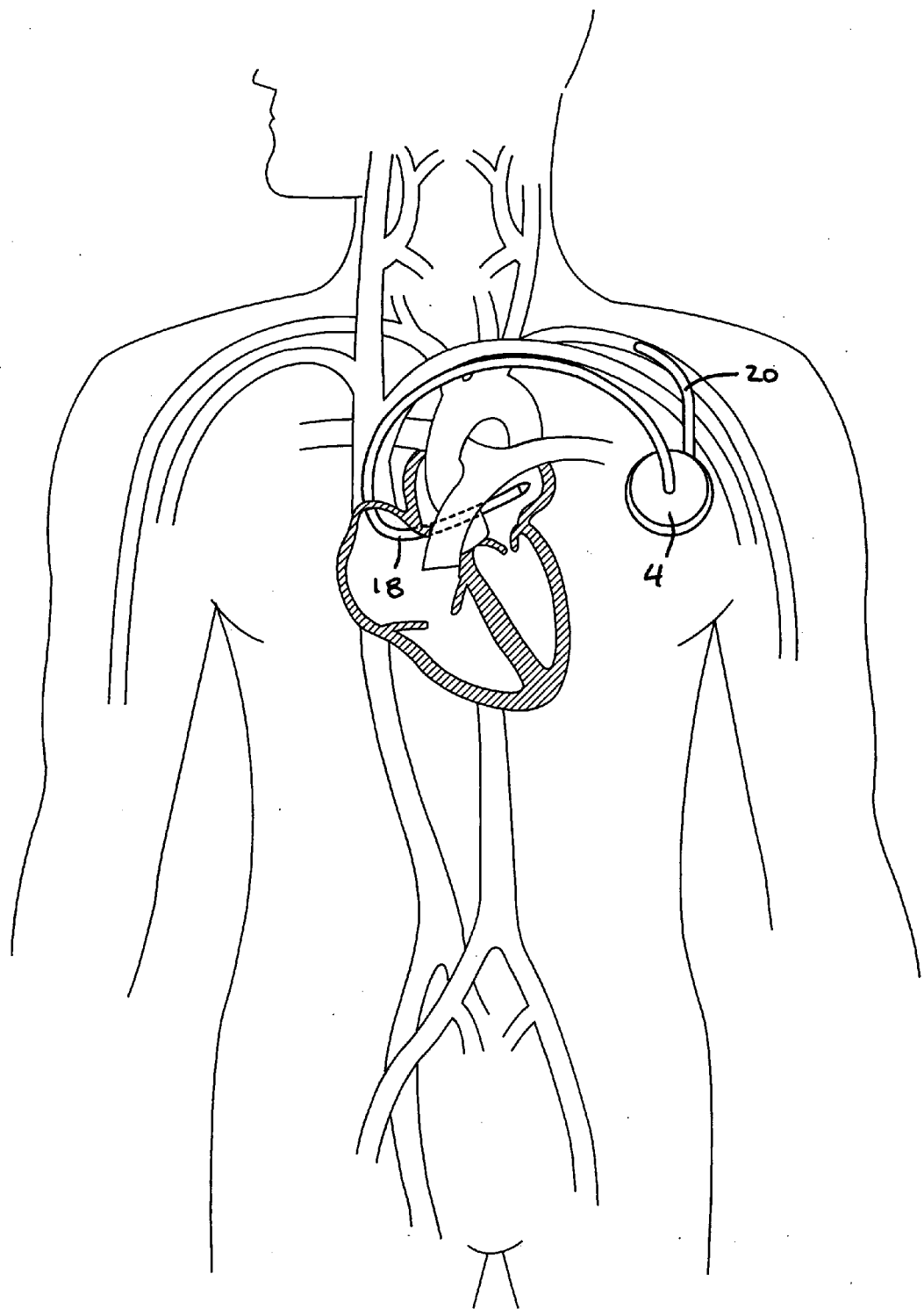
FIG. 6 shows the schematic of FIG. 1 with the pump mounted on the left side of the chest and the pump outlet coupled to the left subclavian artery and the pump inlet coupled to a conduit passing through the SVC, into the right atrium and into the left atrium via the atrial septum.

In still another aspect of the invention, the outlet lumen 20 preferably delivers blood to an axillary or subclavian artery. FIG. 4 shows the outlet lumen 20 coupled to the right axillary or subclavian artery while FIGS. 5 and 6 show the outlet lumen 20 coupled to the left axillary or subclavian artery. The inlet and outlet lumens 18, 20 may be coupled to the target vessels in any suitable manner. For example, the lumens 18, 20 may be coupled to the target vessels with suture, staples or a mechanical coupling. Furthermore, the lumens 18, 20 may extend through the vessels or the lumens 18, 20 may be coupled to the target vessel with an anastomotic connection so that the lumens 18, 20 do not extend through the blood vessels. As mentioned below, various aspects of the invention may be practiced independently. For example, the transseptal approach described above may be used with any other suitable implantable pump and/or system without departing from the scope of the invention. Furthermore, the term "coupling" one of the lumens 18, 20 to a vessel may mean either an anastomotic connection or may mean a connection with the lumens 18, 20 extending through a penetration in the vessel and endovascularly through the vessel. The term "passing" shall mean endovascularly passing the lumen 18, 20 through the vascular system.

In still another aspect of the present invention, the implantable pump 4 is preferably implanted in the following manner. Referring to FIG. 6, the inlet lumen 18 draws blood from the left atrium. The inlet lumen passes through a penetration in the left axillary or subclavian vein and then down the superior vena cava to the right atrium. The inlet lumen 18 then passes through the atrial septum to the left atrium. The outlet lumen 20 preferably delivers blood to the left subclavian or axillary artery.

In still another aspect of the present invention, the implantable pump 4 is preferably implanted in the following manner. Referring to FIG. 7, the inlet lumen 18 draws blood from the left atrium. The inlet lumen passes through a penetration in the right femoral vein, through the superior vena cava and into the right atrium. The inlet lumen 18 then passes through the atrial septum to the left atrium. The outlet lumen 20 preferably delivers the blood to the right femoral artery.

The invention has been described in connection with a various preferred embodiments, however, it is understood that the scope of the invention is not limited to the specific embodiment and many changes and alterations may be made to the preferred embodiment while still remaining within the scope of the invention. For example, any other pump may be used, other vessels may be accessed, the pump may be implanted in other locations and other fluids may be pumped all without departing from various aspects of the invention. Furthermore, although the invention specifically describes a limited number of embodiments, other embodiments are within the scope of the invention and, in particular, use of axillary and subclavian veins and arteries. Thus, the preferred embodiment and description does not limit the scope of the invention.

What is claimed is:

1. A method of providing pumping assistance to a patient's heart, comprising the steps of:
   providing a blood pump having a blood inlet, a blood outlet, and a pumping element;
   implanting the blood pump in a patient;
   coupling the blood inlet to a first vascular location and coupling the blood outlet to a second vascular location selected from axillary and subclavian arteries;

driving the blood pump with an external driver which is coupled to the pumping element by direct magnetic coupling so that blood is drawn into the blood inlet and pumped to the blood outlet and back to the patient to provide pumping assistance to the patient's heart; and recharging a battery with energy generated by the pumping element, wherein the battery can drive the pumping element when the pumping element is not being driven by the external driver.

2. The method of claim 1, further comprising the step of:

passing an inlet lumen through a penetration in a vessel, into the right atrium, through the atrial septum and into the left atrium, the inlet lumen being coupled to the blood inlet of the blood pump.

3. The method of claim 1, wherein:

the implanting step is carried out with the pump being implanted at a subpectoral region outside the patient's ribs.

4. The method of claim 1, wherein:

the coupling step is carried out with the second vascular location being the left axillary or subclavian artery.

5. The method of claim 1, wherein:

the coupling step is carried out with the second vascular location being the right axillary or subclavian artery.

6. The method of claim 4 or 5, wherein:

the coupling step is carried out with the first vascular location being the right axillary or subclavian vein.

7. The method of claim 4 or 5 wherein:

the coupling step is carried out with the first vascular location being the left axillary or subclavian vein.

8. An implantable pump system, comprising:

a pump including:
  (a) a housing;
  (b) a pumping element contained within the housing;
  (c) a blood inlet;
  (d) a blood outlet;
  (e) a pumping element;
  (f) a blood inlet lumen coupled to the blood inlet, the blood inlet lumen being sized and configured to extend through a peripheral vessel to the right atrium, through the atrial septum and into the left atrium, the blood inlet lumen having at least one opening for drawing blood from the left atrium;
  (g) a battery; and an external driver adapted to directly magnetically couple to the pumping element to drive said pumping element wherein the battery is recharged by energy generated by the pumping element and the battery can drive the pumping element when the pumping element is not being driven by the external driver.

* * * * *